(12) United States Patent
Altwasser et al.

(10) Patent No.: US 9,212,157 B2
(45) Date of Patent: Dec. 15, 2015

(54) CATALYST FOR THE OXIDATION OF O-XYLENE AND/OR NAPHTHALENE TO PHTHALIC ANHYDRIDE

(75) Inventors: Stefan Altwasser, Wachenheim (DE); Jürgen Zühlke, Speyer (DE); Frank Rosowski, Mannheim (DE); Michael Krämer, Mannheim (DE)

(73) Assignee: BASF SE, Ludwigshafen (DE)

( * ) Notice: Subject to any disclaimer, the term of this patent is extended or adjusted under 35 U.S.C. 154(b) by 209 days.

(21) Appl. No.: 13/194,126

(22) Filed: Jul. 29, 2011

(65) Prior Publication Data

US 2012/0029214 A1 Feb. 2, 2012

Related U.S. Application Data

(60) Provisional application No. 61/369,087, filed on Jul. 30, 2010.

(51) Int. Cl.
*B01J 23/22* (2006.01)
*C07D 307/89* (2006.01)
*B01J 35/00* (2006.01)
*B01J 35/10* (2006.01)
*B01J 37/00* (2006.01)
*B01J 35/02* (2006.01)

(52) U.S. Cl.
CPC ............ *C07D 307/89* (2013.01); *B01J 23/22* (2013.01); *B01J 35/002* (2013.01); *B01J 35/1014* (2013.01); *B01J 37/0045* (2013.01); *B01J 35/026* (2013.01)

(58) Field of Classification Search
CPC .................... B01J 23/22; C07D 307/89
See application file for complete search history.

(56) References Cited

U.S. PATENT DOCUMENTS

| | | | |
|---|---|---|---|
| 3,560,441 A * | 2/1971 | Schwarcz ...................... 524/405 |
| 4,096,094 A * | 6/1978 | Blechschmitt et al. ....... 502/218 |
| 4,284,571 A | 8/1981 | Sato et al. |
| 4,481,304 A | 11/1984 | Sato et al. |
| 5,792,719 A | 8/1998 | Eberle et al. |
| 5,969,160 A | 10/1999 | Lindstrom |
| 6,288,273 B1 | 9/2001 | Heidemann et al. |
| 6,362,345 B1 | 3/2002 | Heidemann et al. |
| 6,528,683 B1 | 3/2003 | Heidemann et al. |
| 6,586,361 B1 | 7/2003 | Heidemann et al. |
| 6,700,000 B1 | 3/2004 | Heidemann et al. |
| 7,371,893 B2 | 5/2008 | Storck et al. |
| 2006/0235232 A1 * | 10/2006 | Neto et al. ...................... 549/248 |
| 2006/0276661 A1 | 12/2006 | Storck et al. |
| 2007/0060758 A1 | 3/2007 | Storck et al. |
| 2007/0135302 A1 | 6/2007 | Neto et al. |
| 2009/0163726 A1 | 6/2009 | Wilmer et al. |
| 2009/0286999 A1 | 11/2009 | Wilmer et al. |
| 2009/0306409 A1 | 12/2009 | Guckel et al. |
| 2009/0312562 A1 | 12/2009 | Guckel et al. |
| 2009/0318712 A1 | 12/2009 | Wilmer et al. |
| 2010/0069659 A1 | 3/2010 | Raichle et al. |
| 2010/0069660 A1 | 3/2010 | Raichle et al. |
| 2011/0028740 A1 | 2/2011 | Dobner et al. |
| 2011/0034707 A1 | 2/2011 | Wilmer et al. |
| 2011/0118487 A1 | 5/2011 | Abdallah et al. |
| 2011/0124885 A1 | 5/2011 | Altwasser et al. |
| 2011/0130273 A1 | 6/2011 | Karpov et al. |
| 2011/0144387 A1 | 6/2011 | Wentink et al. |
| 2011/0152433 A1 | 6/2011 | Bechtloff et al. |
| 2011/0163278 A1 | 7/2011 | Domke et al. |
| 2011/0195347 A1 | 8/2011 | Querner et al. |
| 2011/0206753 A1 | 8/2011 | Karpov et al. |
| 2011/0230668 A1 | 9/2011 | Altwasser et al. |
| 2011/0245392 A1 | 10/2011 | Karpov et al. |
| 2011/0250124 A1 | 10/2011 | Kramer et al. |
| 2011/0251052 A1 | 10/2011 | Kramer et al. |
| 2011/0251405 A1 | 10/2011 | Altwasser et al. |
| 2011/0257413 A1 | 10/2011 | Dobner et al. |
| 2011/0257414 A1 | 10/2011 | Dobner et al. |
| 2012/0004425 A1 | 1/2012 | Altwasser et al. |
| 2012/0043537 A1 | 2/2012 | Karpov et al. |
| 2012/0071671 A1 | 3/2012 | Karpov et al. |
| 2012/0077998 A1 | 3/2012 | Seeber et al. |
| 2012/0086002 A1 | 4/2012 | Fleischhaker et al. |
| 2012/0097068 A1 | 4/2012 | Riggs et al. |
| 2012/0106139 A1 | 5/2012 | Ewald et al. |
| 2012/0108713 A1 | 5/2012 | Ewald et al. |
| 2012/0149919 A1 | 6/2012 | Altwasser et al. |

FOREIGN PATENT DOCUMENTS

| | | |
|---|---|---|
| DE | 1269119 B | 5/1968 |
| DE | 20 05 969 A1 | 8/1971 |
| DE | 2948163 A1 | 6/1980 |
| DE | 40 06 935 A1 | 9/1991 |
| DE | 4109387 A1 | 9/1992 |
| DE | 198 07 018 A1 | 8/1998 |
| DE | 198 24 532 A1 | 12/1999 |
| DE | 19839001 A1 | 3/2000 |
| EP | 286448 A2 | 10/1988 |
| EP | 522871 A1 | 1/1993 |

(Continued)

OTHER PUBLICATIONS

Valentinite, 2013, http://webmineral.com/data/Valentinite.shtml.*
Senarmontite, 2013, http://www.webmineral.com/data/Senarmontite.shtml.*
Valentinite-date, 2013, http://web.archive.org/web/*/http://webmineral.com/data/Valentinite.shtml.*

(Continued)

*Primary Examiner* — Sun Jae Yoo
(74) *Attorney, Agent, or Firm* — Drinker Biddle & Reath LLP

(57) ABSTRACT

The present invention relates to a catalyst for the oxidation of o-xylene and/or naphthalene to phthalic anhydride, which has a plurality of catalyst zones which are arranged in series in the reaction tube and have been produced using an antimony trioxide which comprises a significant proportion of valentinite. The present invention further relates to a process for gas-phase oxidation, in which a gas stream comprising at least one hydrocarbon and molecular oxygen is passed through a catalyst produced using an antimony trioxide which comprises a significant proportion of valentinite.

13 Claims, No Drawings

(56) References Cited

FOREIGN PATENT DOCUMENTS

| EP | 539878 A2 | 5/1993 |
|---|---|---|
| EP | 0 744 214 A1 | 11/1996 |
| EP | 1082317 A1 | 3/2001 |
| EP | 1084115 A1 | 3/2001 |
| EP | 1091806 A1 | 4/2001 |
| EP | 1636161 A1 | 3/2006 |
| EP | 2009520 A1 | 12/2008 |
| WO | WO-2004103561 A1 | 12/2004 |
| WO | WO-2004103943 A1 | 12/2004 |
| WO | WO-2005030388 A1 | 4/2005 |
| WO | WO-2006125468 A1 | 11/2006 |
| WO | WO-2007116018 A1 | 10/2007 |
| WO | WO-2007134849 A1 | 11/2007 |
| WO | WO-2010/136551 A2 | 12/2010 |
| WO | WO-2011/080051 A1 | 7/2011 |

OTHER PUBLICATIONS

Senarmontite, 2013, http://web.archive.org/web/*/http://www.webmineral.com/data/Senarmontite.shtml.*
U.S. Appl. No. 13/518,768.
Stanislaw E. Golunski et al., "Antimony Oxides : a Guide to Phase Changes During Catalyst Preparation", Applied Catalysis, vol. 48, pp. 123-135, 1989.
U. A. Schubert et al., "Possible effects of site isolation in antimony oxide-modified vanadia/titania catalysts for selective oxidation of o-xylene", Topics in Catalysis, vol. 15, No. 2-4, pp. 195-200, 2001.
Christer Svensson, "Refinement of the Crystal Structure of Cubic Antimony Trioxide, $Sb_2O_3$", Aeta Cryst., vol. B31, pp. 2016-2018, 1975.
Howard E.Swanson et al., "Standard X-ray Diffraction Powder Patterns", National Bureau of Standards Circular 539, vol. 10, pp. 6-8, 1960.
International Search Report from companion PCT/EP2010/067432 of Nov. 15, 2010.
International Search Resort from PCT/IB2011/053327 dated Jan. 5, 2012.
International Search Report for PCT/IB2011/052831.
Anastasov, A. I., "Deactivation of an industrial $V_2O_5$—$TiO_2$ catalyster for oxidation ofo-xylene into phthalic anhydride," Chemical Engineering and Processing, 2003, vol. 42, pp. 449-460.
Bond, G. C., "What Limits the Selectivity Attainable in the Catalysed Oxidation of o-Xylene to Phthalic Anhydride?" J. Chem. Tech. Biotechnol., 1997, vol. 68, pp. 6-13.
Galantowicz, M., et al., "Effect of thermal deactivation of vanadium—titanium catalyst on o-xylene oxidation process yielding phthalic anhydride," Studies in Surface Science and Catalysis, 1994, vol. 88, pp. 591-596.
Garcin, et al., "Preparation of $V_2O_5$/$TiO_2$ Eurocat oxide catalysts," *Catalysis Today* 20 (1994), pp. 7-10.
Grzybowska-Świerkosz, "Vanadia-titania catalysts for oxidation of o-xylene and other hydrocarbons," *Applied Catalysis A: General* 157 (1997), pp. 263-310.
International Search Report from PCT/IB2011/053327 dated Jan. 5, 2012.

* cited by examiner

CATALYST FOR THE OXIDATION OF O-XYLENE AND/OR NAPHTHALENE TO PHTHALIC ANHYDRIDE

CROSS-REFERENCE TO RELATED APPLICATIONS

This application claims benefit (under 35 USC 119(e)) of U.S. Provisional Application 61/369,087, filed Jul. 30, 2010 which is incorporated by reference.

BACKGROUND OF THE INVENTION

The present invention relates to a catalyst for the oxidation of o-xylene and/or naphthalene to phthalic anhydride, which has a plurality of catalyst zones which are arranged in series in the reaction tube and have been produced using an antimony trioxide which comprises a significant proportion of valentinite. The present invention further relates to a process for gas-phase oxidation, in which a gas stream comprising at least one hydrocarbon and molecular oxygen is passed through a catalyst produced using an antimony trioxide which comprises a significant proportion of valentinite.

Many carboxylic acids and/or carboxylic anhydrides are prepared industrially by catalytic gas-phase oxidation of hydrocarbons such as benzene, xylenes, naphthalene, toluene or durene in fixed-bed reactors. In this way, it is possible to obtain, for example, benzoic acid, maleic anhydride, phthalic anhydride, isophthalic acid, terephthalic acid or pyromellitic anhydride. In general, a mixture of an oxygen-comprising gas and the starting material to be oxidized is passed through tubes in which a bed of a catalyst is present. To regulate the temperature, the tubes are surrounded by a heat transfer medium, for example a salt melt.

Coated catalysts in which the catalytically active composition has been applied in the form of a shell to an inert support material such as steatite have been found to be useful as catalysts for these oxidation reactions. In general, the catalysts have a layer of active composition which has an essentially homogeneous chemical constitution and has been applied in the form of a shell. Furthermore, two or more different layers of active composition can be applied in succession to a support. These are then referred to as two-layer or multilayer catalysts (see, for example, DE 19839001 A1).

As catalytically active constituents of the catalytically active composition of these coated catalysts, use is generally made of titanium dioxide and vanadium pentoxide. Furthermore, small amounts of many other oxidic compounds which act as promoters to influence the activity and selectivity of the catalyst, including cesium oxide, phosphorus oxide and antimony oxide, can be present in the catalytically active composition.

Catalysts giving a particularly high PAn yield can, according to EP 1636161, be obtained when particular $V_2O_5/Sb_2O_3$ ratios are set and the antimony trioxide has a defined average particle size.

The presence of antimony oxides leads to an increase in the PAn selectivity; the effect is considered to be separation of the vanadium sites.

The antimony oxides used in the active composition of the catalysts can be various antimony(III), antimony(IV) and antimony(V) compounds; antimony trioxide or antimony pentoxide are usually used. EP 522871 describes the use of antimony pentoxide, US 2009/306409 and EP 1636161 disclose the use of antimony trioxide.

Compared to antimony tetroxide and antimony pentoxide, antimony trioxide has the ability to spread better on titanium dioxide, so that significantly improved distribution of the catalyst is achieved. Antimony trioxide is typically used as pure senarmontite phase (cf. Schubert, U.-A. et al., Topics in Catalysis, 2001, vol. 15(2-4), pages 195 to 200). Apart from the cubic senarmontite, there is also an orthorhombic modification of antimony trioxide, known as valentinite (Golunski, S. E. et al., Appl. Catal., 1989, vol. 48, pages 123 to 135).

There is a continual need for catalysts for gas-phase oxidations, which catalysts give a very high conversion at high selectivity.

BRIEF SUMMARY OF THE INVENTION

It is an object of the present invention to develop a catalyst for the oxidation of o-xylene and/or naphthalene to phthalic anhydride, which catalyst makes possible a high phthalic anhydride yield with a low o-xylene and phthalide content at a low salt bath temperature.

This object is achieved by a catalyst for the oxidation of o-xylene and/or naphthalene to phthalic anhydride, which has been produced using an antimony trioxide which comprises a significant proportion of valentinite.

It is an object of the invention to provide a catalyst for the oxidation of o-xylene and/or naphthalene to phthalic anhydride, which has been produced using an antimony trioxide in which the ratio of signal height in the X-ray powder diffraction pattern at 2-theta=28.4° to the sum of the signal heights at 2-theta=27.7° and 28.4° is at least 0.02.

DETAILED DESCRIPTION OF THE INVENTION

The signal at 2-theta=27.7° is characteristic of senarmontite (cf. ASTM Index, No. 5-0534/7) and the signal at 2-theta=28.4° for valentinite (cf. ASTM Index, No. 11-689). The signal height is given by the difference between the maximum intensity of the respective signal and the background determined.

In a preferred embodiment of the invention, the catalyst has been produced using an antimony trioxide in which the ratio of the signal height in the X-ray powder diffraction pattern at 2-theta=28.4° to the sum of the signal heights at 2-theta=27.7° and 28.4° is at least 0.03, particularly preferably at least 0.05.

The antimony trioxide to be used according to the invention having a significant valentinite content can be used for producing one or more catalyst zones. In a preferred embodiment of the invention, the catalyst has three, four or five zones, with antimony trioxide having a significant valentinite content having been used for producing at least one zone.

The catalysts of the invention can, for example to avoid high hot spot temperatures, also be used in combination with suitable upstream and/or downstream beds and also together with intermediate zones, with the upstream and/or downstream beds and the intermediate zones generally being able to comprise catalytically inactive or less active material.

The catalysts of the invention are generally coated catalysts in which the catalytically active composition has been applied in the form of a shell to an inert support material.

As inert support material, it is possible to use virtually all support materials of the prior art as are advantageously used in the production of coated catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The catalyst supports can, for example, be used in the form of spheres, rings, pellets, spirals, tubes, extrudates or crushed material. The dimensions of these catalyst supports correspond to those of catalyst supports usually used for producing coated catalysts for gas-phase reactions of aromatic hydrocarbons. Preference is given to using steatite in the form of spheres having a diameter of from 3 to 6 mm or of rings having an external diameter of from 5 to 9 mm and a length of from 3 to 8 mm and a wall thickness of from 1 to 2 mm.

The catalysts of the invention comprise a catalytically active composition which comprises at least vanadium oxide and titanium dioxide and can be applied in one or more layers to the support material. Various layers can in this case differ in terms of their chemical constitution.

The catalytically active composition preferably comprises, based on the total amount of the catalytically active composition, from 1 to 40% by weight of vanadium oxide, calculated as $V_2O_5$, and from 60 to 99% by weight of titanium dioxide, calculated as $TiO_2$. The catalytically active composition can, in preferred embodiments, additionally comprise up to 1% by weight of a cesium compound, calculated as Cs, up to 1% by weight of a phosphorus compound, calculated as P, and up to 10% by weight of antimony oxide, calculated as $Sb_2O_3$. All figures relating to the chemical constitution of the catalytically active composition are based on the calcined state of the latter, e.g. after calcination of the catalyst for one hour at 450° C.

Titanium dioxide is usually used in the anatase form for the catalytically active composition. The titanium dioxide preferably has a BET surface area of from 15 to 60 $m^2/g$, in particular from 15 to 45 $m^2/g$, particularly preferably from 13 to 28 $m^2/g$. The titanium dioxide used can be an individual titanium dioxide or a mixture of titanium dioxides. In the latter case, the magnitude of the BET surface area as weighted average determines the contributions of the individual titanium dioxides. The titanium dioxide used is, for example, advantageously a mixture of a $TiO_2$ having a BET surface area of from 5 to 15 $m^2/g$ and a $TiO_2$ having a BET surface area of from 15 to 50 $m^2/g$.

Suitable vanadium sources are, in particular, vanadium pentoxide or ammonium metavanadate. Suitable antimony sources are various antimony trioxides which have a significant valentinite content. Possible phosphorus sources are, in particular, phosphoric acid, phosphorous acid, hypophosphorous acid, ammonium phosphate or phosphoric esters and especially ammonium dihydrogenphosphate. Suitable sources of cesium are the oxide or hydroxide or the salts which can be converted thermally into the oxide, e.g. carboxylates, in particular the acetate, malonate or oxalate, carbonate, hydrogencarbonate, sulfate or nitrate.

Apart from the optional additions of cesium and phosphorus, the catalytically active composition can comprise small amounts of many other oxidic compounds which act as promoters to influence the activity and selectivity of the catalyst, for example by decreasing or increasing its activity. Examples of such promoters are the alkali metals, in particular lithium, potassium and rubidium in addition to the abovementioned cesium, which are usually used in the form of their oxides or hydroxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony tetroxide, antimony pentoxide and cerium oxide.

Furthermore, among the abovementioned promoters, further preference is given to the oxides of niobium and tungsten as additives in amounts of from 0.01 to 0.50% by weight, based on the catalytically active composition.

The application of the layer(s) of the coated catalyst is advantageously carried out by spraying a suspension of $TiO_2$ and $V_2O_5$, which optionally comprises sources of the abovementioned promoter elements, onto the fluidized support. Before coating, the suspension is preferably stirred for a sufficiently long time, e.g. from 2 to 30 hours, in particular from 12 to 25 hours, in order to break up agglomerates of the suspended solids and obtain a homogeneous suspension. The suspension typically has a solids content of from 20 to 50% by weight. The suspension medium is generally aqueous, e.g. water itself or an aqueous mixture with a water-miscible organic solvent such as methanol, ethanol, isopropanol, formamide and the like.

In general, organic binders, preferably copolymers, advantageously in the form of an aqueous dispersion, of acrylic acid-maleic acid, vinyl acetate-vinyl laurate, vinyl acetate-acrylate, styrene-acrylate and vinyl acetate-ethylene, are added to the suspension. The binders are commercially available as aqueous dispersions having a solids content of, for example, from 35 to 65% by weight. The amount of such binder dispersions used is generally from 2 to 45% by weight, preferably from 5 to 35% by weight, particularly preferably from 7 to 20% by weight, based on the weight of the suspension.

The support is fluidized in an ascending gas stream, in particular air, in, for example, a fluidized-bed apparatus or a moving-bed apparatus. The apparatuses usually comprise a conical or spherical vessel into which the fluidizing gas is introduced from below or from above via an immersed tube. The suspension is sprayed through nozzles into the fluidized bed from above, from the side or from below. The use of a riser pipe arranged centrically or concentrically around the immersed tube is advantageous. A higher gas velocity which transports the support particles upward prevails within the riser pipe. In the outer ring, the gas velocity is only a little above the loosening velocity. As a result, the particles are moved vertically in a circular fashion. A suitable fluidized-bed apparatus is described, for example, in DE-A 4006935.

Coating temperatures of from 20 to 500° C. are generally employed in coating of the catalyst support with the catalytically active composition, with coating being able to be carried out under atmospheric pressure or under reduced pressure. In general, coating is carried out at from 0° C. to 200° C., preferably from 20 to 150° C., in particular from 60 to 120° C.

The layer thickness of the catalytically active composition is generally from 0.02 to 0.2 mm, preferably from 0.05 to 0.15 mm. The proportion of active composition in the catalyst is usually from 5 to 25% by weight, mostly from 7 to 15% by weight.

Thermal treatment at temperatures of from >200 to 500° C. of the precatalyst obtained in this way results in the binder being given off from the applied layer due to thermal decomposition and/or combustion. The thermal treatment is preferably carried out in situ in the gas-phase oxidation reactor.

The invention further provides a process for gas-phase oxidation, wherein a gas stream comprising at least one hydrocarbon and molecular oxygen is passed through a catalyst produced using an antimony trioxide in which the ratio of the signal height in the X-ray powder diffraction pattern at 2-theta=28.4° to the sum of the signal heights at 2-theta=27.7° and 28.4° is at least 0.02.

A preferred embodiment of the invention is a process for the gas-phase oxidation of o-xylene and/or naphthalene to phthalic anhydride, wherein a gas stream comprising o-xylene and/or naphthalene and molecular oxygen is passed through a catalyst produced using an antimony trioxide in which the ratio of the signal height in the X-ray powder diffraction pattern at 2-theta=28.4° to the sum of the signal heights at 2-theta=27.7° and 28.4° is at least 0.02.

EXAMPLES

Determination of the valentinite content and the senarmontite content in antimony trioxide: The determination was carried out by means of X-ray powder diffractometry. For this purpose, the antimony trioxide powder was measured in a "D5000 Theta/Theta" X-ray powder diffractometer from Siemens. The measurement parameters were as follows:

| | |
|---|---|
| Diameter | 435 mm |
| X-radiation | CuK-alpha ($\lambda = 1.54 \cdot 10^{-10}$ m) |
| Tube voltage | 40 kV |
| Tube current | 30 mA |
| Aperture | Variable V20 |
| Scattered radiation orifice | Variable V20 |
| Secondary monochromator | Graphite |
| Monochromator aperture | 0.1 mm |
| Scintillation counter | |
| Detector aperture | 0.6 mm |
| Step width | 0.02° 2Θ |
| Step mode | Continuous |
| Measurement time | 2.4 s/step |
| Measurement rate | 0.5° 2Θ/min |

The signal height is given by the difference between the maximum intensity of the respective signal and the background determined. To determine the valentinite content, the signals at 2-theta=27.7° (senarmontite, signal height a) and 28.4° (valentinite, signal height b) were employed. The valentinite content is b/(a+b), and the senarmontite content is a/(a+b).

Example 1

According to the Invention

Catalyst Zone CZ1:
3.38 g of cesium carbonate, 459.3 g of titanium dioxide (Fuji TA 100C, anatase, BET surface area 20 m$^2$/g), 196.9 g of titanium dioxide (Fuji TA 100, anatase, BET surface area 7 m$^2$/g) and 51.4 g of vanadium pentoxide and 13.2 g of antimony trioxide (Merck Selectipur 7835, valentinite content=0.18, senarmontite content=0.82, 99.5% $Sb_2O_3$ content, 300 ppm by weight of As, 500 ppm by weight of Pb, 50 ppm by weight of Fe, average particle size 2 μm) were suspended in 1869 g of demineralized water and stirred for 18 hours to achieve a homogeneous distribution. 78.4 g of organic binder comprising a copolymer of vinyl acetate and vinyl laurate were added in the form of a 50% strength by weight aqueous dispersion to this suspension. In a fluidized-bed apparatus, 820 g of this suspension were sprayed onto 2 kg of steatite (magnesium silicate) in the form of rings having dimensions of 7 mm×7 mm×4 mm and dried. After calcination of the catalyst for one hour at 450° C., the amount of active composition applied to the steatite rings was 9.1%. The analyzed chemical constitution of the active composition was 7.1% of $V_2O_5$, 1.8% of $Sb_2O_3$, 0.38% of Cs, balance $TiO_2$.
Catalyst Zone CZ2:
Production analogous to CZ1 with variation of the chemical constitution of the suspension. After calcination of the catalyst for one hour at 450° C., the amount of active composition applied to the steatite rings was 8.5%. The analyzed chemical constitution of the active composition comprised 7.95% of $V_2O_5$, 2.7% of $Sb_2O_3$, 0.31% of Cs, balance $TiO_2$ having an average BET surface area of 18 m$^2$/g.
Catalyst Zone CZ3:
Production analogous to CZ1 with variation of the chemical constitution of the suspension. After calcination of the catalyst for one hour at 450° C., the amount of active composition applied to the steatite rings was 8.5%. The analyzed chemical constitution of the active composition comprised 7.1% of $V_2O_5$, 2.4% of $Sb_2O_3$, 0.10% of Cs, balance $TiO_2$ having an average BET surface area of 17 m$^2$/g.
Catalyst Zone CZ4:
Production analogous to CZ1 with variation of the chemical constitution of the suspension and using Fuji TA 100CT, anatase, BET surface area 27 m$^2$/g, instead of Fuji TA 100C. After calcination of the catalyst for one hour at 450° C., the amount of active composition applied to the steatite rings was 9.1%. The analyzed chemical constitution of the active composition comprised 20% of $V_2O_5$, 0.38% of P, balance $TiO_2$ having an average BET surface area of 23 m$^2$/g.

Example 2

Not According to the Invention

Catalyst Zone CZ5:
Production analogous to CZ1 but using an antimony trioxide grade having a reduced valentinite content (e.g. Triox white from Antraco, valentinite content=0.015, senarmontite content=0.985, 99.3% $Sb_2O_3$ content, 0.3% by weight of $As_2O_3$, 0.18% by weight of PbO, 0.02% by weight of iron oxide, average particle size 1.5 μm).
Catalyst Zone CZ6:
Production analogous to CZ2 but using an antimony trioxide grade having a reduced valentinite content (e.g. Triox white from Antraco, valentinite content=0.015, senarmontite content=0.985, 99.3% $Sb_2O_3$ content, 0.3% by weight of $As_2O_3$, 0.18% by weight of PbO, 0.02% by weight of iron oxide, average particle size 1.5 μm).
Catalyst Zone CZ7:
Production analogous to CZ3 but using an antimony trioxide grade having a reduced valentinite content (e.g. Triox white from Antraco, valentinite content=0.015, senarmontite content=0.985, 99.3% $Sb_2O_3$ content, 0.3% by weight of $As_2O_3$, 0.18% by weight of PbO, 0.02% by weight of iron oxide, average particle size 1.5 μm).

Example 3

Oxidation of o-Xylene to Phthalic Anhydride on the Model Tube Scale, According to the Invention The catalytic oxidation of o-xylene to phthalic anhydride was carried out in a salt bath-cooled tube reactor having an internal diameter of the tubes of 25 mm. From the reactor inlet to the reactor outlet, 130 cm of CZ1, 70 cm of CZ2, 60 cm of CZ3 and 60 cm of CZ4 were introduced into an iron tube having a length of 3.5 m and an internal diameter of 25 mm. The iron tube was surrounded by a salt melt to regulate the temperature; a thermocouple sheath having an external diameter of 4 mm and a built-in withdrawable element served to measure the catalyst temperature.
4.0 standard m$^3$/h of air having loadings of 99.2% strength by weight o-xylene of from 30 to 100 g/standard m$^3$ were passed through the tube from the top downward. This gave the results summarized in table 1 ("PAn yield" is the amount of phthalic anhydride obtained in percent by weight, based on 100% strength o-xylene).

Example 4

Oxidation of o-Xylene to Phthalic Anhydride on the Model Tube Scale, not According to the Invention See example 3, but with a catalyst bed comprising, from the reactor inlet to the reactor outlet, 130 cm of CZ5, 70 cm of CZ6, 60 cm of CZ7 and 60 cm of CZ4.

TABLE 1

| Model tube results | Example 3 (according to the invention) | | Example 4 (not according to the invention) | |
|---|---|---|---|---|
| Amount of air [standard m³/h] | 4.0 | 4.0 | 4.0 | 4.0 |
| Loading [g/standard m³] | 70 | 82 | 72 | 81 |
| Running time [days] | 33 | 40 | 21 | 29 |
| Salt bath temperature [° C.] | 352.0 | 347.0 | 357.0 | 352.0 |
| PAn yield [% by weight] | 112.5 | 113.0 | 111.5 | 112.5 |
| o-Xylene content [% by weight] | 0.03 | 0.08 | 0.03 | 0.07 |
| Phthalide content [% by weight] | 0.05 | 0.09 | 0.06 | 0.10 |

Comparison of examples 3 and 4 in table 1 shows that the catalyst activity of the catalyst in example 3 is higher than that in example 4. The salt bath temperature in example 3 (according to the invention) can for this reason be lowered further, and the PSn yield with a low o-xylene and phthalide content is significantly higher than in example 4 (not according to the invention).

Example 5

Oxidation of o-Xylene to Phthalic Anhydride on an Industrial Scale, According to the Invention The catalytic oxidation of o-xylene to phthalic anhydride was carried out in a salt bath-cooled tube reactor having 15 105 tubes having an internal diameter of the tubes of 25 mm. From the reactor inlet to the reactor outlet, 130 cm of CZ1, 90 cm of CZ2, 60 cm of CZ3 and 60 cm of CZ4 were introduced. To record temperature profiles, some reactor tubes were equipped with a thermocouple. 4.0 standard m³/h of air having an o-xylene loading (purity about 99% by weight) of from 0 to 100 g/standard m³ were passed through the tubes. The PAn yields were measured in the reactor outlet gas and are reported in table 2 in % by weight (kg of PAn per kg of o-xylene reacted) based on 100% strength o-xylene.

Example 6

Oxidation of o-Xylene to Phthalic Anhydride on an Industrial Scale, not According to the Invention See example 5, but with a catalyst bed from reactor inlet to reactor outlet comprising 130 cm of CZ5, 90 cm of CZ6, 60 cm of CZ7 and 60 cm of CZ4.

TABLE 2

| Industrial scale | Example 5 (according to the invention) | Example 6 (not according to the invention) |
|---|---|---|
| Amount of air [standard m³/h] | 4.0 | 4.0 |
| Loading [g/standard m³] | 95 | 95 |
| Running time [days] | 79 | 76 |
| Salt bath temperature [° C.] | 343.4 | 346.2 |
| PAn yield [% by weight] | 114.5 | 112.9 |
| o-Xylene content [% by weight] | 0.08 | 0.06 |
| Phthalide content [% by weight] | 0.01 | 0.01 |

Comparison of examples 5 and 6 in table 2 shows that the catalyst activity of the catalyst in example 5 is higher than that in example 6. The salt bath temperature in example 5 (according to the invention) can for this reason be lowered further, and the PAn yield with a low o-xylene and phthalide content is significantly higher than in example 6 (not according to the invention).

The invention claimed is:

1. A catalyst for the oxidation of o-xylene and/or naphthalene to phthalic anhydride comprising titanium dioxide, vanadium pentoxide and antimony trioxide and at least three catalyst zones, wherein the catalyst of at least one zone is produced by a process comprising an antimony trioxide in which the ratio of signal height in the X-ray powder diffraction pattern at 2-theta=28.4° to the sum of the signal heights at 2-theta=27.7° and 28.4° is at least 0.02 and is thermally treated at from 200 to 500° C.

2. A process for gas-phase oxidation comprising passing a gas stream comprising at least one hydrocarbon and molecular oxygen through a catalyst according to claim 1.

3. The process according to claim 2, wherein the hydrocarbon is o-xylene and/or naphthalene.

4. The process according to claim 2, wherein the hydrocarbon is o-xylene.

5. The process according to claim 2, wherein the hydrocarbon is naphthalene.

6. The process according to claim 2, wherein the hydrocarbon is o-xylene and naphthalene.

7. The catalyst according to claim 1, wherein the thermal treatment is carried out in situ in a gas-phase oxidation reactor.

8. The catalyst according to claim 1, wherein the catalyst comprises at least four catalyst zones.

9. The catalyst according to claim 1, wherein the catalyst comprises at least five catalyst zones.

10. The catalyst according to claim 1, wherein the catalyst is applied in the form of a shell to an inert support material.

11. The catalyst according to claim 10, wherein the inert support material is in the form a spheres, rings, pellets, spirals, tubes, extrudates or crushed material.

12. The catalyst according to claim 1, wherein the catalyst further comprises up to 1% by weight of a cesium compound, calculated as Cs.

13. The catalyst according to claim 1, wherein the catalyst further comprises up to 1% by weight of a phosphorous compound, calculated as P.

* * * * *